United States Patent
Woehrmann et al.

(10) Patent No.: US 10,583,072 B2
(45) Date of Patent: Mar. 10, 2020

(54) COSMETIC SHAVING STICK

(71) Applicant: BEIERSDORF AG, Hamburg (DE)

(72) Inventors: Michael Woehrmann, Norderstedt (DE); Julia Gerjets, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 134 days.

(21) Appl. No.: 15/628,720

(22) Filed: Jun. 21, 2017

(65) Prior Publication Data

US 2018/0325790 A1   Nov. 15, 2018

(30) Foreign Application Priority Data

May 11, 2017   (DE) .................... 20 2017 002 510 U

(51) Int. Cl.
| | | |
|---|---|---|
| *A61K 8/46* | (2006.01) | |
| *A61K 8/34* | (2006.01) | |
| *A61K 8/36* | (2006.01) | |
| *A61K 8/02* | (2006.01) | |
| *A61Q 9/02* | (2006.01) | |
| *A61Q 19/00* | (2006.01) | |

(52) U.S. Cl.
CPC ............ *A61K 8/463* (2013.01); *A61K 8/0229* (2013.01); *A61K 8/345* (2013.01); *A61K 8/361* (2013.01); *A61K 8/466* (2013.01); *A61Q 9/02* (2013.01); *A61Q 19/00* (2013.01); *A61K 2800/87* (2013.01)

(58) Field of Classification Search
None
See application file for complete search history.

(56) References Cited

U.S. PATENT DOCUMENTS 5,294,438 A * 3/1994 Chang .................. A61K 8/90
424/401

FOREIGN PATENT DOCUMENTS

| EP | 0623338 A2 | 11/1994 |
|---|---|---|
| WO | 9637185 A1 | 11/1996 |

* cited by examiner

*Primary Examiner* — Nannette Holloman
(74) *Attorney, Agent, or Firm* — Abel Schillinger, LLP

(57) ABSTRACT

Disclosed is a cosmetic product comprising a cosmetic stick composition that comprises one or more fatty acids and/or salts thereof, one or more anionic surfactants selected from alkyl sulfates, alkyl ether sulfates and alkylbenzenesulfonates, and glycerol as well as an application container which contains the stick composition.

20 Claims, No Drawings

COSMETIC SHAVING STICK

CROSS-REFERENCE TO RELATED APPLICATIONS

The present application claims priority under 35 U.S.C. § 119 of German Utility Model Application No. 20 2017 002 510.8, filed May 11, 2017, the entire disclosure of which is expressly incorporated by reference herein.

BACKGROUND OF THE INVENTION

1. Field of the Invention

The present invention relates to a cosmetic product, a shaving stick comprising a cosmetic stick composition that comprises one or more fatty acids and/or salts thereof, one or more sulfate surfactants and glycerol; and an application container from which the cosmetic stick composition is applied to the skin.

2. Discussion of Background Information

A beautiful and attractive appearance is a desire of many people. In this case, a pure and groomed skin is often an ideal of beauty. In order to conform to this, a wide variety of different cosmetic products for daily cleansing and care of the body are used.

For a flawless appearance, there exists nowadays a need for cosmetic reasons to remove body hair from the face, from the chest, from the abdomen, from the back, in the bikini zone or private parts, from the legs and underarms. Since removal by the known hair removal methods such as waxes or epilation is usually linked to pain, classical wet shaving is enjoying great popularity.

To enable as pleasant a shave as possible, it is usual to apply a cosmetic shaving product to the body part in question prior to shaving in order to improve the lubricating properties of the razor blade on the skin. Moreover, the cosmetic shaving product should cause the individual hairs to become softer and thus to be able to be cut easily without the blade tugging directly on the surface of the skin.

In particular, shaving foams are known which are produced by foaming a soap-containing preparation with propellant. Furthermore, there are shaving gels which are withdrawn from a pressurized container and are applied to the skin. These contain gases with a high boiling point, typically isopentanes. As soon as the gel comes into contact with warm skin, the propellant present starts to evaporate which leads to foaming of the preparation.

Another class of cosmetic shaving products, which are not based on the use of propellants, are shaving creams. For application, these are mostly foamed with a moistened shaving brush and distributed on facial skin with the brush. These preparations are also generally based on soaps, water-soluble fatty acid salts for example, especially lauric acid, myristic acid, palmitic acid, stearic acid and so on.

The cosmetic shaving products described above often have numerous disadvantages as regards shaving on the chest, the abdomen, the back, in the bikini zone or private parts, on the legs and underarms. For instance, extensive application of aerosol products is not sensible since these products have only a limited spreading power. Daily application of aerosol-based shaving foams on extensive areas of the body therefore leads to high consumption, and therefore more economical product forms for the consumer are desirable.

The same problems also arise with application of shaving creams. Moreover, these have the disadvantage that they have to be foamed such that application for shaving of large body regions is time-consuming. Accordingly, product forms are desirable which can be readily and rapidly applied and require no further processing steps.

Classical solid shaving soaps are also known which are mostly produced based on fatty acid salts and coconut oil. In order to ensure sufficient foam formation, it is necessary to foam these products with a moistened shaving brush. Separately, also known are shaving sticks which are intended to be applied directly from an applicator to the skin previously wetted with water. In the case of this cosmetic shaving product, a film or a minimal amount of foam is transferred to the skin by rubbing. A typical shaving stick is known, inter aria, under the Mintel entry number 3910965 (Boots Original Shave Stick). This shaving stick also consists in large part of soap constituents but does not contain any sulfate surfactants.

The major advantage of shaving sticks is that these can be applied simply and rapidly to the whole body and are therefore very economical. Accordingly, there is not the problem as in shaving creams and shaving foams foamed with propellant which are rapidly consumed. Moreover, shaving sticks are generally compact and there is sometimes no need for a shaving brush for foaming such that these can be taken along when travelling, saving space. A further advantage consists in that no additional means, such as the hand, which is then sticky and often has to be washed, or brushes, are required for application and distribution on the skin.

Nevertheless, these advantages must not disguise the fact that shaving sticks have numerous disadvantages, which accounts for their minor role in the mass market of cosmetic shaving products.

Firstly, shaving sticks often have the disadvantage that they are perceived by the consumer as unpleasantly hard on the skin whereas shaving foams foamed with propellant are soft and gentle on the skin. Furthermore, the amount of rubbing required and the film formation and/or foam formation on the skin often leave much to be desired and are unsatisfactory.

Another cause of annoyance, which often occurs when using shaving sticks of the prior art, is that, due to the rather compact film and/or foam on the skin when shaving with shaving systems with several blades in the razor, such as Nivea Protect & Shave pivoting joint razor, rapid blockage of the razor blades may result. For instance, the cut hair gets in between the blades with the soap constituents and can be washed out again only with difficulty. A simple body shave can therefore become a stressful experience.

When using shaving sticks of the prior art it may also happen that soap constituents, despite rinsing the skin with water, remain there after shaving and leave behind white stripes for example. This is to be avoided.

In view of the foregoing, it would be advantageous to have available a cosmetic shaving stick which does not have the disadvantages of the known products.

EP 0623338 A2 and WO 9637185 A 1, the entire disclosures of which are incorporated by reference herein, both disclose stick compositions containing surfactants. No stick compositions with sulfate surfactants is disclosed however.

SUMMARY OF THE INVENTION

The present invention provides a cosmetic product that comprises (a) a cosmetic stick composition comprising, based on the total weight of the stick composition
   (i) from about 10% to about 25% by weight of one or more fatty acids having a saturated or unsaturated, linear or branched alkyl group having from about 8 to about 20 carbon atoms and/or salts thereof;
   (ii) from about 8% to about 25% by weight of one or more anionic surfactants selected from one or more of
   alkyl sulfates and alkyl ether sulfates of formula

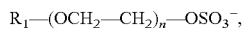
   $R_1-(OCH_2-CH_2)_n-OSO_3^-$, where $R_1$ is a saturated or unsaturated, linear or branched alkyl group having from about 8 to about 24 carbon atoms, n=0 or an integer of from 1 to about 12, and $M^+$ is an alkali metal ion, alkaline earth metal ion and/or an ammonium ion, and alkylbenzenesulfonates of formula

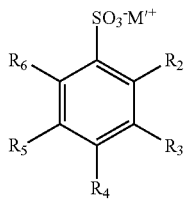

where $R_2$, $R_3$, $R_4$, $R_5$ and $R_6$ each independently represent a hydrogen atom or an alkyl group having from 1 to about 12 carbon atoms, at least one of $R_2$, $R_3$, $R_4$, $R_5$ and $R_6$ being different from hydrogen, and $M'^+$ is an alkali metal ion, alkaline earth metal ion and/or an ammonium ion;
   and
   (iii) from about 8% to about 20% by weight, preferably from about 10% to about 15% by weight, of glycerol; and
(b) an application container containing the cosmetic stick composition which is configured for allowing an application of the stick composition to the skin.

The present invention further provides a method of pretreating the skin for shaving. The method comprises applying the cosmetic stick composition to skin wetted with water prior to shaving, preferably from about 5 seconds to about 2 minutes prior to shaving.

The present invention further provides a method in which, in a first step, the cosmetic stick composition is applied from the application container to skin wetted with water and, in a second step, the hair is shaved with a blade.

It has been shown, surprisingly, that when using the product according to the invention for shaving, the disadvantages of the prior art can be remedied. For instance, inter alia, it has been established, surprisingly, that when used for shaving on skin previously wetted with water, the razor blades in shaving systems with four or more blades are blocked significantly less. In this case, residues in the razor heads can be particularly easily rinsed off. The stick composition also has the effect that the blades glide particularly easily over the skin.

It has been found, moreover, that the rubbing of the cosmetic product is particularly gentle on the skin and that an amount sufficient for shaving can be transferred particularly easily onto the skin. Also, the residues of the rubbing can be particularly easily rinsed off the skin.

All percentages by weight (% by weight) listed below, unless stated otherwise, refer to the total weight of the cosmetic stick composition in each case.

Unless stated otherwise, all experiments were conducted under standard conditions. The term "standard conditions" indicates 20° C., 1013 hPa and a relative humidity of 50%.

In the context of the present disclosure, the expression "free of" indicates that the proportion of the respective substance is less than 0.05% by weight, preferably less than 0.01% by weight. It is thereby ensured that introductions or impurities with these substances are not included as "free of" in accordance with the invention.

If the expression "skin" is used in the present disclosure, this refers exclusively to human skin.

The cosmetic stick composition of the present invention comprises in accordance with the invention, based on the total weight of the cosmetic stick composition, from about 10% to about 25% by weight of one or more fatty acids having a saturated or unsaturated, linear or branched alkyl group having from about 8 to about 20 carbon atoms and/or salts thereof.

It is preferred in accordance with the invention in this case, if the total proportion of the fatty acids and/or salts thereof having a saturated or unsaturated, linear or branched alkyl group having from about 8 to about 20 carbon atoms is from about 12% to about 20% by weight, particularly preferably from about 13% to about 19% by weight, based on the total weight of the cosmetic stick composition.

It is advantageous in accordance with the invention if the fatty acids and/or salts thereof according to the invention are selected from one or more of lauric acid, myristic acid, palmitic acid, stearic acid, isostearic acid, oleic acid and linoleic acid and/or corresponding salts thereof.

If fatty acids are used in accordance with the invention, these are preferably selected from one or more of lauric acid (dodecanoic acid), myristic acid (tetradecanoic acid), palmitic acid (hexadecanoic acid) and stearic acid (octadecanoic acid).

If salts of fatty acids are used, these are preferably selected from sodium, potassium and/or triethanolamine salts of the above fatty acids.

In the context of the present invention, it is particularly preferable if one or more of the following fatty acid salts are present: triethanolamine stearate (INCI: TEA-Stearate), triethanolamine palmitate (INCI: TEA-Palmitate), triethanol myristate (INCI: TEA-Myristate), triethanol laurate (INCI: TEA-Laurate), potassium stearate, potassium palmitate, potassium myristate, potassium laurate, sodium stearate, sodium palmitate, sodium myristate and sodium laurate.

In addition to the pure fatty acids and/or salts thereof, it is also possible in accordance with the invention to use optionally chemically modified mixtures of fatty acids and/or salts thereof from natural sources. Such mixtures comprising fatty acids or salts thereof may be obtained, for example, from fats and oils such as tallow, coconut oil, palm oil, olive oil, laurel oil or rapeseed oil. Typical examples of INCI substances which comprise the fatty acid salts for use according to the invention are, for example, sodium cocoate or sodium tallowate. For these substances, the relevant active content of fatty acid salts according to the invention is to be taken into account. For example, sodium cocoate comprises the salts sodium laurate, sodium myristate, sodium palmitate, sodium stearate and sodium oleate.

The cosmetic stick composition according to the invention also comprises, based on the total weight of the cosmetic stick composition, from about 8% to about 25% by weight, preferably from about 10% to about 20% by weight and particularly preferably from about 12% to about 18% by weight of one or more anionic surfactants selected from the following:

alkyl sulfates and alkyl ether sulfates of the formula $R_1-(OCH_2-CH_2)_n-OSO_3^-M^+$, where $R_1$ is a saturated or unsaturated, linear or branched alkyl group having from about 8 to about 24 carbon atoms, n=0 or an integer of from 1 to about 12, and $M^+$ represents an alkali metal ion, alkaline earth metal ion and/or an ammonium ion, and alkylbenzenesulfonates according to the formula

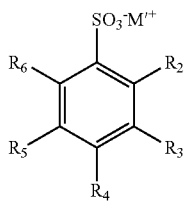

where $R_2$, $R_3$, $R_4$, $R_5$ and $R_6$ each independently represents a hydrogen atom or an alkyl group having from 1 to about 12 carbon atoms, at least one of $R_2$, $R_3$, $R_4$, $R_5$ and $R_6$ being different from hydrogen, and where $M^{'+}$ represents an alkali metal ion, alkaline earth metal ion and/or an ammonium ion.

Ethoxylated and non-ethoxylated sulfate surfactants may be present in the cosmetic stick composition in combination. Examples of ethoxylated sulfate surfactants suitable for use according to the invention include, among others, sodium myristyl ether sulfate, sodium lauryl ether sulfate and ammonium lauryl ether sulfate. Known representatives of the non-ethoxylated sulfate surfactants suitable for use according to the invention are, among others, ammonium lauryl sulfate, sodium lauryl sulfate and sodium coco sulfate.

The alkylbenzenesulfonates suitable for use in accordance with the invention comprise at least one alkyl group as substituent of the benzene ring. In the cosmetic stick composition according to the invention, preferably present are sodium 2,4-dimethylbenzenesulfonate and/or sodium dodecylbenzenesulfonate as representative of the group of alkylbenzenesulfonates. With particular preference, sodium 2,4-dimethylbenzenesulfonate is selected, which is known under the INCI name Sodium Xylene Sulfonate.

Advantageous cosmetic stick compositions according to the invention accordingly comprise one or more anionic surfactants selected from sodium myristyl ether sulfate, sodium lauryl ether sulfate, ammonium lauryl ether sulfate, ammonium lauryl sulfate, sodium lauryl sulfate, sodium coco sulfate and sodium 2,4-dimethylbenzenesulfonate.

In this case (and also in general), it is particularly advantageous if the proportion by weight of ethoxylated anionic surfactants to non-ethoxylated anionic surfactants is from about 2:1 to about 1:2, preferably from about 1.5:1 to about 1:1.5. Such a mixture of surfactants has proved to be particularly mild to the skin and does not cause any skin irritations. At the same time, the combination enables a particularly uniform wetting of the skin with the cosmetic stick composition.

The cosmetic stick composition according to the invention also comprises from about 8% to about 20% by weight, preferably from about 10% to about 15% by weight, of glycerol, based on the total weight of the cosmetic stick composition.

The combination according to the invention of fatty acids and/or salts thereof, the surfactants specified and glycerol leads to the advantages listed compared to the shaving preparations known from the prior art. Particularly advantageously, the stick compositions additionally have the specific penetration force values elucidated below as a measure of the strength of the sticks.

Penetration force values may be stated in g. A penetration force value of 1 g indicates that the force which a mass of 1 g exerts has to be used in order to introduce the impactor corresponding to the measurement parameters into the cosmetic stick composition.

Advantageously, the cosmetic stick compositions according to the invention 24 h after preparation of the stick composition are characterized by exhibiting at 20° C. a penetration force value in the range of from about 20 g to about 120 g, preferably from about 50 g to about 100 g, particularly preferably from about 60 g to about 80 g. If the penetration force value is within the above limits, it has been shown that the stick composition when rubbed on skin wetted with water is perceived as neither too hard nor too soft. Instead, the mass of the cosmetic stick composition is experienced as particularly creamy and pleasant. Surprisingly, the cosmetic stick composition in the preferred range of penetration force values can be transferred particularly easily to the skin to be shaved. It has been found that such cosmetic stick compositions exhibit a particularly efficient deposition and swelling on short stubble having a length of up to about 2 mm.

In accordance with the invention, the penetration force value of cosmetic stick compositions is determined as follows: Using a TA-XT2i Texture Analyzer from Stable Micro Systems (Godalming, Surrey, UK), a stainless steel needle (impactor) of 1 mm diameter is used, having a pointed cone with a tapering of 18" and a cone length of 5.5 mm. The measurement is conducted at the following speeds:

i) 1 mm/s up to the point of contact with the impactor
ii) 2 mm/s is the measurement speed
iii) 10 mm/s is the speed of the needle on withdrawal.

The triggering force for the measurement is 5 g. On inserting the impactor into the cosmetic stick composition, it is determined which maximum force has to be applied in order to enable the impactor to penetrate 5.000 mm deep into the cosmetic stick composition with the speed of advance specified above. The maximum force applied corresponds to the penetration force value. The greater the penetration force value, the more solid is the stick composition. The penetration force value is measured according to the invention at an ambient temperature of 20° C. and 50% relative humidity. A measurement is only valid if the cosmetic stick composition does not break.

Cosmetic stick compositions which can be applied particularly well and readily to the skin are advantageously characterized by exhibiting a dimensionally stable consistency at application temperatures which may range from about −20° C. to about +50° C. This means that the stick composition should not flow in this temperature range. The yield limit or yield point is a designation for the smallest shear stress above which a plastic substance behaves rheologically as a liquid (DIN 1342-1: 1983-10). The yield limit is determined by recording a flow curve (derived according to DIN 53019: 1980-05; DIN 53214: 1982-02). Cosmetic stick compositions according to the invention therefore have a yield limit above the temperature range.

The cosmetic stick composition is present in an application container for application of the stick composition to the skin. Such an application container has at least one opening via which the cosmetic stick composition can be transferred to the skin by rubbing. It is advantageous in this case if the application container has a mechanism by means of which the cosmetic stick composition can be moved out through the opening. An application container of this kind has the advantage that after rubbing of the upper layer of the cosmetic stick composition, this can be further withdrawn from the opening so that further rubbing is possible. Such application containers are extensively known in the prior art for lip balm sticks or deodorant sticks, e.g. Nivea Dry Impact Stick.

The cosmetic stick composition is advantageously stored in the application container on a sealed or partially unsealed platform, which can move the cosmetic stick composition in the application container in the direction of the opening by means of a screw thread.

It is also advantageous if the application container has a cover, which can seal the opening for applying the cosmetic stick composition to the skin.

If the platform on which the cosmetic stick composition is stored in the application container is unsealed, or rather has at least one opening, it is possible to fill the cosmetic stick composition through the at least one opening in the platform and to use the cover of the application container as shaping element for the cosmetic stick composition. For a filling of this kind, the cosmetic stick composition is warmed so that this becomes flowable, and in this state is poured through the at least one opening in the platform. After cooling, a solid cosmetic stick composition is obtained which can be moved with the platform in the application container.

The stick composition according to the invention in stick form preferably has a cylindrical shape having a diameter of from about 3 cm to about 5 cm. In this application size, the extensive application of the stick composition on the skin is performed with only a few application steps which is a decisive advantage compared to customary smaller application sticks.

The cosmetic stick composition according to the invention is further advantageously characterized by comprising from about 25% to about 45% by weight, preferably from about 30% by weight to about 40% by weight of water, based on the total weight of the cosmetic stick composition. Such a high water content enables an effective rubbing of the cosmetic stick composition on the skin.

It is also advantageous if the cosmetic stick composition comprises one or more skin-moistening additives, particularly one or more of methylpropanediol, sorbitol and propylene glycol. Due to the hygroscopic properties, these substances bind moisture to the skin such that the skin feels more elastic and more pleasant to the consumer after shaving.

If sorbitol is present in the cosmetic stick composition according to the invention, the proportion of sorbitol is advantageously from about 5% to about 10% by weight, based on the total weight of the cosmetic stick composition.

If propylene glycol is present in the cosmetic stick composition according to the invention, the proportion of propylene glycol is advantageously from about 7% to about 14% by weight, based on the total weight of the cosmetic stick composition.

Furthermore, it is advantageous in the context of the present invention if the cosmetic stick composition has a pH in the range of from about 9 to about 11, preferably from about 9.5 to about 10.5.

It has also been shown that the cosmetic product according to the invention has particularly pleasant application properties when the cosmetic stick composition has a density at 20° C. of from about 1.0 to about 1.1 $g/cm^3$.

To provide an optically appealing cosmetic stick composition, it is advantageous if color pigments are present in the cosmetic stick composition. A possible color pigment which gives the cosmetic stick composition a whitish appearance is titanium dioxide. This may be added depending on how much an opaque or white cosmetic stick composition is desired.

Furthermore, it can be advantageous if the cosmetic stick composition comprises complexing agents such as ethylenediaminetetraacetic acid.

It is furthermore advantageous if the cosmetic stick composition comprises one or more further active ingredients which care for the skin after and during shaving. Examples of advantageous active ingredients include aloe vera or panthenol.

The cosmetic stick composition is advantageously free of mineral hydrocarbon oils and waxes, such as paraffin oil (paraffinum liquidum), petrolatum or cera microcristallina. In this manner it is ensured that no aromatic hydrocarbons are present in the cosmetic stick composition. In this manner, additionally any skin irritations may be avoided.

Furthermore, the cosmetic stick composition according to the invention is advantageously free of aluminum salts. In this manner, skin irritations, which can be triggered by aluminum salts, can be reduced or prevented. Especially in freshly shaved skin, skin irritations with aluminum salts may occur on contact with small cut wounds. By using aluminum-free stick compositions, absorption of aluminum through small cut wounds is excluded.

A further advantage of the present invention is that it is possible, surprisingly, to provide a cosmetic product containing a cosmetic stick composition which is free of preservatives, without microbial instabilities occurring on storage of the stick composition at 40° C. and 50% humidity. The cosmetic stick composition according to the invention is therefore advantageously free of preservatives.

Preservatives are those preserving substances which, according to the German Cosmetics Directive and according to Regulation (EC) No, 1223/2009 on cosmetic agents, are approved for use in cosmetic products in Europe.

When applying the stick composition according to the invention on skin wetted with water, it is particularly advantageous if the stick composition is pre-swelled with warm water having a temperature of from about 30° C. to about 40° C. immediately prior to applying to the skin wetted with water. This means for example, keeping the stick composition under flowing water for about 10 to about 30 seconds or dipping it under water for the same time period.

DETAILED DESCRIPTION OF EXEMPLARY EMBODIMENTS

The following examples are intended to illustrate the present invention without limiting it. Unless otherwise stated, all quantitative data, fractions and percentages are based on the weight and the total amount or total weight of the cosmetic stick compositions.

| INCI | Ex. 1 | Ex. 2 | Ex. 3 | Ex. 4 |
| --- | --- | --- | --- | --- |
| Propylene Glycol | 9.5 | 8.9 | 11.1 | 10.1 |
| Sodium Stearate | 9.5 | 8.7 | 9.7 | 9.3 |
| Sodium Laureth Sulfate | 7.6 | 10.1 | 9.8 | 7.1 |
| Glycerol | 12.6 | 18.1 | 14.5 | 11.8 |

-continued

| INCI | Ex. 1 | Ex. 2 | Ex. 3 | Ex. 4 |
|---|---|---|---|---|
| Sorbitol | 7.6 | 5.2 | 8.1 | 6.9 |
| Sodium Cocoate | 5.7 | 6.3 | 5.4 | 6.1 |
| Sodium Xylene Sulfonate | 5.7 | 3.0 | 6.0 | 5.2 |
| Sodium Lauryl Sulfate | 2.3 | 5.0 | 2.0 | 2.2 |
| Stearic Acid | 1.5 | 2.0 | 1.8 | 1.3 |
| Tetra Sodium EDTA | 0.04 | — | 0.1 | 0.06 |
| Tetra Sodium Etidronate | 0.03 | 0.1 | — | 0.02 |
| Titanium Dioxide | 0.03 | 0.08 | 0.01 | 0.1 |
| Panthenol | 0.7 | 0.2 | 0.9 | 0.3 |
| Aloe Barbadensis Leaf Juice Powder | 0.01 | 0.02 | 0.01 | 0.01 |
| Perfume | 0.8 | 1.5 | 0.3 | 0.6 |
| Aqua | to 100 | to 100 | to 100 | to 100 |

The cosmetic product according to the invention is obtained by melting the ingredients and, after mixing, directly filling the molten mass into the application container. After cooling to room temperature, the cosmetic product according to the invention is obtained. The cosmetic stick composition according to Example I has a penetration force value of 66.3 g.

What is claimed is:

1. A cosmetic product comprising
   (a) a cosmetic stick composition comprising in by weight based on a total weight of the stick composition
      (i) from 10% to 25% of one or more fatty acids having a saturated or unsaturated, linear or branched alkyl group having from 8 to 20 carbon atoms and/or one or more salts thereof;
      (ii) from 8% to 25% by weight of one or more anionic surfactants selected from one or more of
      alkyl sulfates and alkyl ether sulfates of formula

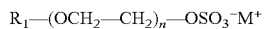
      $R_1-(OCH_2-CH_2)_n-OSO_3^-M^+$ where $R_1$ is a saturated or unsaturated, linear or branched alkyl group having from 8 to 24 carbon atoms, n=0 or an integer of from 1 to 12, and $M^+$ is an alkali metal ion, alkaline earth metal ion and/or an ammonium ion, and
      alkylbenzenesulfonates of formula

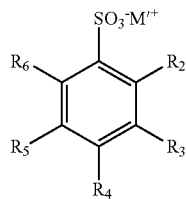

where $R_2$, $R_3$, $R_4$, $R_5$ and $R_6$ each independently represent hydrogen or an alkyl group having from 1 to 12 carbon atoms, at least one of $R_2$, $R_3$, $R_4$, $R_5$ and $R_6$ being different from hydrogen, and $M'^+$ is an alkali metal ion, alkaline earth metal ion and/or an ammonium ion; and
      (iii) from 8% to 20% by weight of glycerol; and
   (b) an application container comprising the cosmetic stick composition.

2. The cosmetic product of claim 1, wherein a total proportion of (i) in the cosmetic stick composition is from 12% to 20%.

3. The cosmetic product of claim 1, wherein a total proportion of (i) in the cosmetic stick composition is from 13% to 19%.

4. The cosmetic product of claim 1, wherein (i) comprises one or more of lauric acid, myristic acid, palmitic acid, stearic acid, isostearic acid, oleic acid and linoleic acid and/or one or more salts of these acids.

5. The cosmetic product of claim 1, wherein (i) comprises one or more of triethanolamine stearate, triethanolamine palmitate, triethanol myristate, triethanol laurate, potassium stearate, potassium palmitate, potassium myristate, potassium laurate, sodium stearate, sodium palmitate, sodium myristate, sodium laurate.

6. The cosmetic product of claim 1, wherein the composition comprises from 10% to 20% by weight of (ii).

7. The cosmetic product of claim 1, wherein the composition comprises from 12% to 18% by weight of (ii).

8. The cosmetic product of claim 1, wherein (ii) comprises one or more of sodium myristyl ether sulfate, sodium lauryl ether sulfate, ammonium lauryl ether sulfate, ammonium lauryl sulfate, sodium lauryl sulfate, sodium coco sulfate, sodium 2,4-dimethylbenzenesulfonate.

9. The cosmetic product of claim 1, wherein a proportion by weight of ethoxylated anionic surfactants to non-ethoxylated anionic surfactants in (ii) is from 2:1 to 1:2.

10. The cosmetic product of claim 1, wherein a proportion by weight of ethoxylated anionic surfactants to non-ethoxylated anionic surfactants in (ii) is from 1.5:1 to 1:1.5.

11. The cosmetic product of claim 1, wherein the cosmetic stick composition exhibits a penetration force value at 20° C. in a range of from 20 g to 120 g, the penetration force value being determined by driving a stainless steel needle of 1 mm diameter, having a pointed cone with a tapering of 18° and a cone length of 5.5 mm, 5 mm deep into the stick composition at a measurement speed of 2 mm/s.

12. The cosmetic product of claim 1, wherein the cosmetic stick composition comprises from 25% to 45% by weight of water.

13. The cosmetic product of claim 1, wherein the cosmetic stick composition further comprises one or more skin-moistening additives selected from methylpropanediol, sorbitol and propylene glycol.

14. The cosmetic product of claim 1, wherein the stick composition has a pH of from 9 to 11.

15. The cosmetic product of claim 1, wherein the cosmetic stick composition is free of mineral hydrocarbon oils and waxes.

16. The cosmetic product of claim 1, wherein the cosmetic stick composition is free of preservatives.

17. The cosmetic product of claim 1, wherein the cosmetic stick composition is free of aluminum salts.

18. The cosmetic product of claim 1, wherein the cosmetic stick composition has a cylindrical shape having a diameter of from 3 cm to 5 cm.

19. The cosmetic product of claim 1, wherein the cosmetic stick composition further comprises from 7% to 14% by weight of propylene glycol.

20. The cosmetic product of claim 1, wherein the cosmetic stick composition further comprises from 5% to 10% by weight of sorbitol.

* * * * *